(12) United States Patent
Hassan (10) Patent No.: US 12,062,455 B2
(45) Date of Patent: Aug. 13, 2024

(54) CORONAVIRUS REAL-TIME MAP (71) Applicant: Marwan Hassan, Fremont, CA (US)

(72) Inventor: Marwan Hassan, Fremont, CA (US)

( * ) Notice: Subject to any disclaimer, the term of this patent is extended or adjusted under 35 U.S.C. 154(b) by 588 days.

(21) Appl. No.: 17/230,999

(22) Filed: Apr. 15, 2021

(65) Prior Publication Data

US 2021/0257107 A1 Aug. 19, 2021

Related U.S. Application Data

(60) Provisional application No. 63/014,691, filed on Apr. 23, 2020.

(51) Int. Cl.
*G16H 50/80* (2018.01)
*G16H 10/60* (2018.01)
*G16H 50/70* (2018.01)
*H04W 64/00* (2009.01)

(52) U.S. Cl.
CPC ............ *G16H 50/80* (2018.01); *G16H 10/60* (2018.01); *G16H 50/70* (2018.01); *H04W 64/003* (2013.01); *H04W 64/006* (2013.01)

(58) Field of Classification Search
CPC ........ G16H 50/80; G16H 10/60; G16H 50/70; H04W 64/003; H04W 64/006
See application file for complete search history.

(56) References Cited

U.S. PATENT DOCUMENTS

| | | | | |
|---|---|---|---|---|
| 7,817,046 | B2 * | 10/2010 | Coveley | H01Q 7/00 340/572.1 |
| 2003/0009356 | A1 * | 1/2003 | Hildebrand | G16H 40/67 705/2 |
| 2003/0204130 | A1 * | 10/2003 | Colston, Jr. | G16H 50/80 600/300 |
| 2012/0112883 | A1 * | 5/2012 | Wallace | G16H 50/80 340/10.1 |
| 2017/0024531 | A1 * | 1/2017 | Malaviya | G16H 50/30 |
| 2017/0352119 | A1 * | 12/2017 | Pittman | G16H 50/80 |
| 2019/0333646 | A1 * | 10/2019 | Shaw | G06F 7/00 |
| 2023/0121997 | A1 * | 4/2023 | Dang | G16H 50/80 382/103 |

FOREIGN PATENT DOCUMENTS

CN 111403045 A * 7/2020

* cited by examiner

*Primary Examiner* — Ryan W Sherwin (57) ABSTRACT

The present invention discloses a coronavirus real-time map to alarm users when approaching infected locations. The infected locations are updated in real-time based on the life cycle of the virus on surfaces, and the virus test results of the users. The data collected about the user's geographic locations are locally stored on the user's mobile phone to secure their personal privacy.

13 Claims, 7 Drawing Sheets

CORONAVIRUS REAL-TIME MAP

This application claims the benefits of a U.S. Provisional Patent Application No. 63/014,691, filed Apr. 23, 2020, titled "Coronavirus Four-Dimensional Map".

BACKGROUND

The location detection of a virus infection is a critical health issue that enables us to avoid infection. To achieve that, most current solutions propose software applications supported by a GPS to track the user's movement or geographic location using his/her mobile phone. For many people, this is not a practical solution because it conflicts with the personal privacy of people that do not accept their personal information being collected and shared with others. In fact, there is a need for a real technological solution that detects the locations of virus infections, without interfering with the personal privacy of the users, to alarm the users when approaching such infected locations.

SUMMARY

The present invention discloses a real-time map for coronavirus and other viruses, to alarm users when approaching potential infected places or locations while walking. The data collected about the user's geographic location and personal information is locally stored on the user's mobile phone and is not accessible to others, which complies with the user's personal privacy. Once the user approaches an infected location, an alarming message is displayed on his/her mobile phone, giving the user routing options to reach his/her final destination without passing by such infected locations.

DETAILED DESCRIPTION

Figure 1:
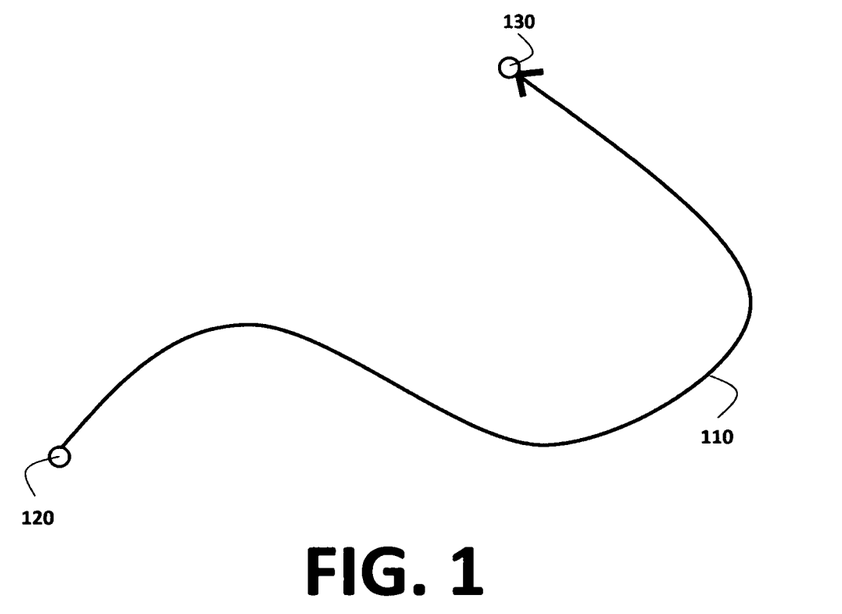
FIG. 1 illustrates a first path of a first user moving from a start point to an end point.
Figure 2:
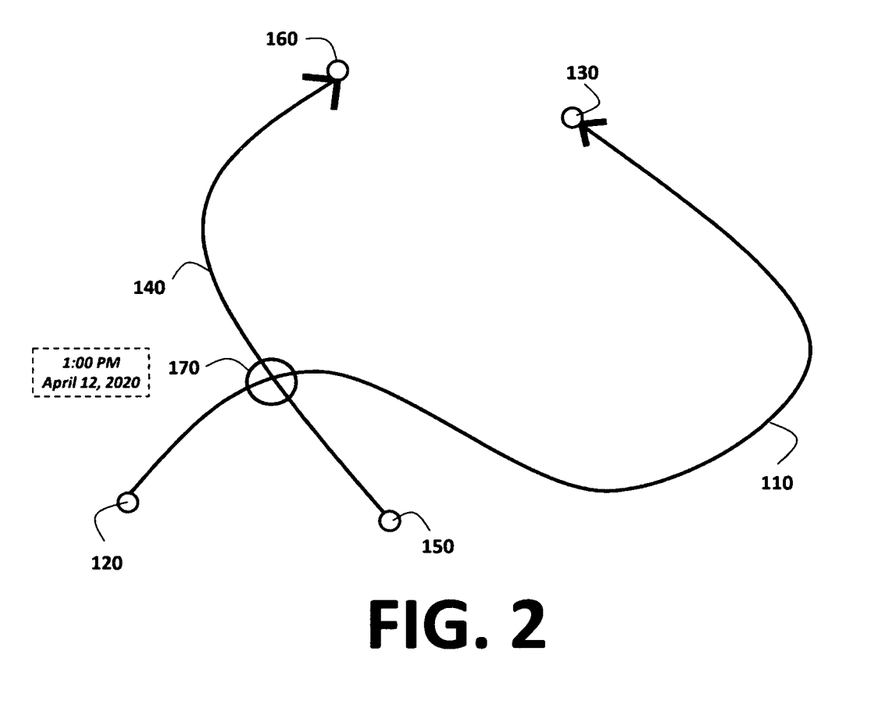
FIG. 2 illustrates a second path of a second user intersecting with the first path at a first point of intersection.

FIG. 1 illustrates an example of a first person's path 110 moving from a start point 120 to an end point 130 over a period of time. FIG. 2 illustrates a second person's path 140 moving from a start point 150 to an end point 160 over a period of time. As shown in the figure, the two paths of the first and second persons intersect with each other at the first intersection point 170. As shown in the figure, the first and second person met at the first intersection point at "1:00 PM on Apr. 12, 2020".

Figure 3:
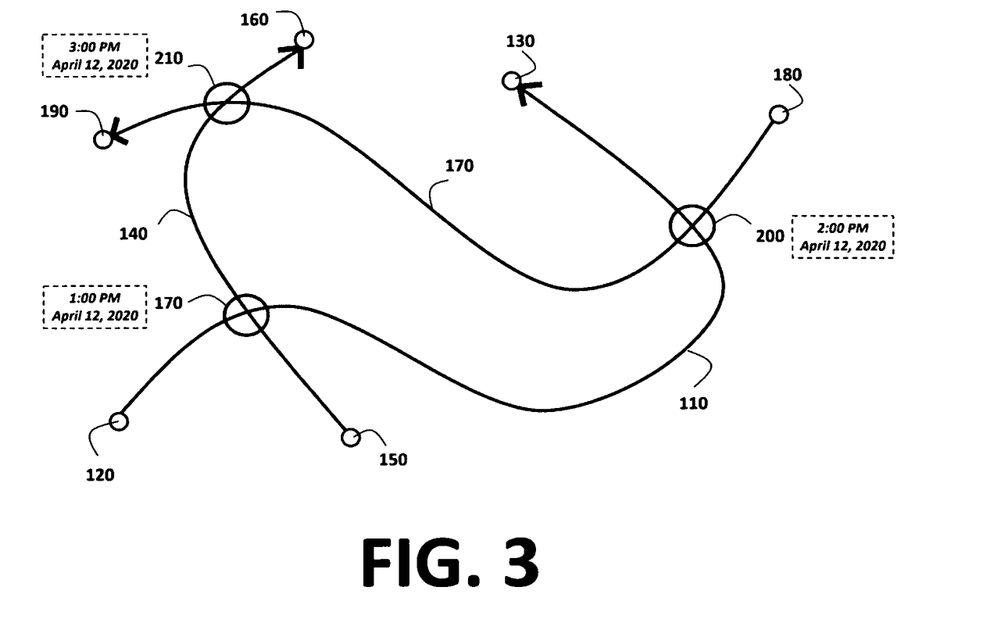
FIG. 3 illustrates a third path of a third user intersecting with the first and second paths at second and third points of intersection.

FIG. 3 illustrates a third person's path 170 moving from a start point 180 to an end point 190. The path of the third person intersects with the two paths of the first and second persons successively at the second intersection point 200 and the third intersection point 210. As shown in the figure, the first and third persons met at the second intersection point at "2:00 PM on Apr. 12, 2020". In addition, the second and third persons met at the second intersection point at "3:00 PM on Apr. 12, 2020".

Figure 4:
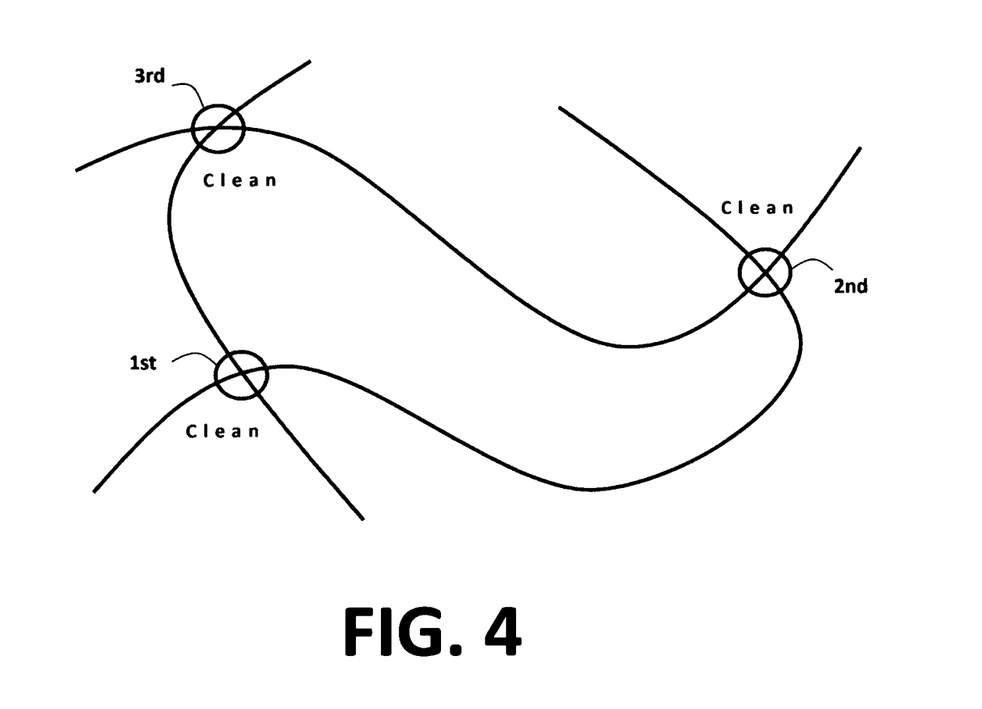
FIG. 4 illustrates tagging the three points of intersections with a "clean" label as an indication for the absence of various infections at these points.
Figure 5:
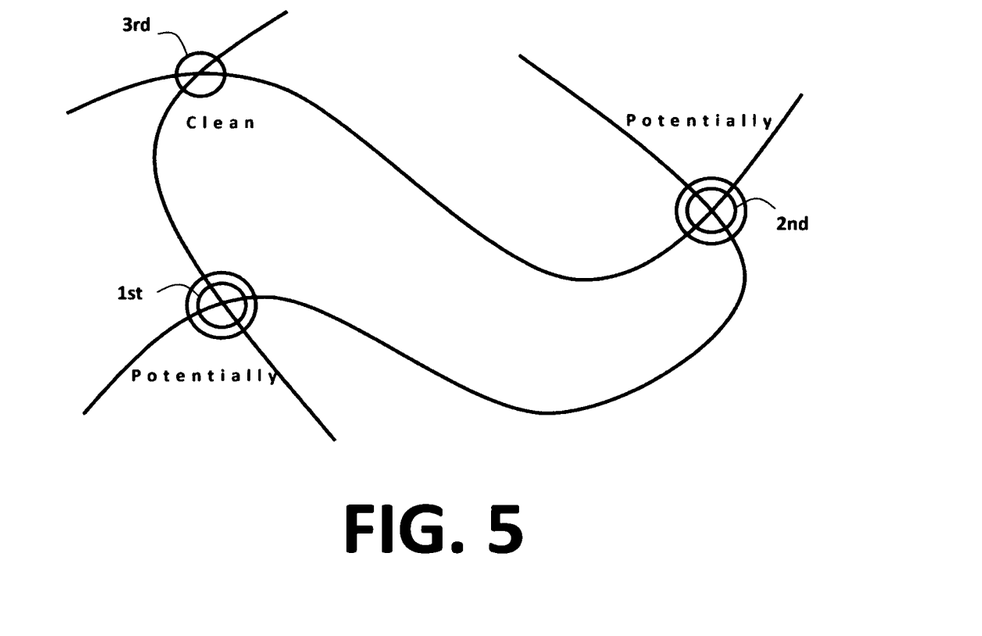
FIG. 5 illustrates tagging two of the three points of intersection with a "potential" label as indication for a potential infection of a virus at these two points.

Theoretically, if the three persons were tested negative for COVID-19, before starting their three paths, in this case, the first, second and third intersection points are tagged as a "clean' point or spot, as shown in FIG. 4. The "clean" tag of a spot means there is no evidence that this spot is infected with a virus. If the first person tested negative before starting their path, and tested positive after ending their path, that means they got infected somewhere on their path. In this case, the first and second interaction points tagged as "potential" infection points, as shown in FIG. 5, whereas the first and second intersection points are located on the path of the first person. The "potential" tag of a spot means there is evidence that this spot might be infected with a virus.

Figure 6:
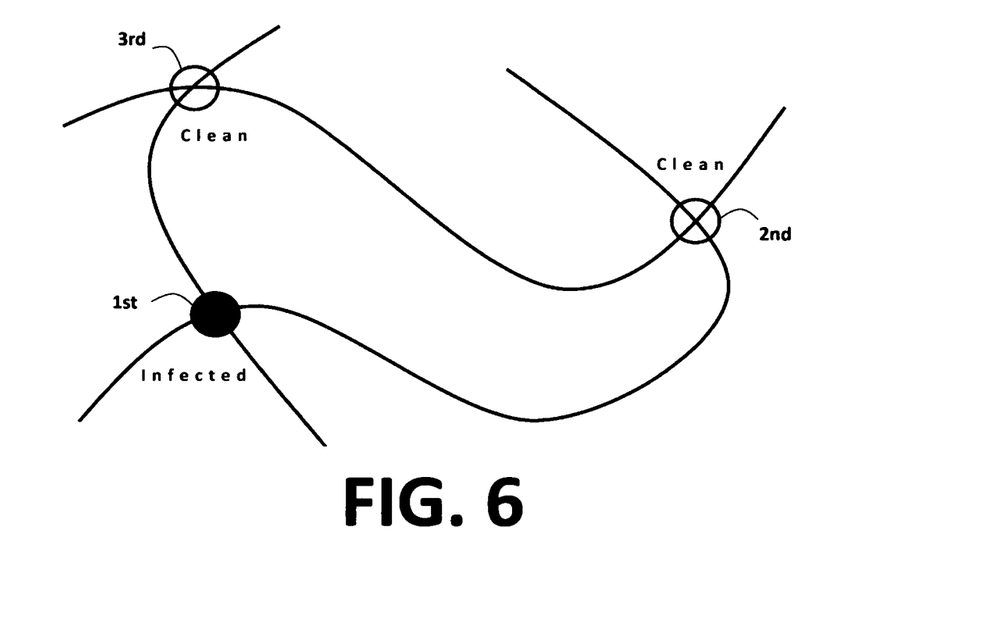
FIG. 6 illustrates tagging a point of the three points of intersection with an "infected" label as indication for the existence of a virus at this point.

If both of the first and second persons tested negative before starting their paths, and tested positive after ending their paths, in this case, the first interaction point is tagged as an "infected" spot, as shown in FIG. 6. In other words, somewhere on the paths of the first and second persons there is an infection point that made them got infected. Since the first intersection point is located on the two paths of the first and second persons, the first intersection point is confirmed to be an infected point. In such a case, the second and third points of intersection are tagged as "clean" points, as shown in the figure.

The clean, potential, and infected points are related to places that may infect people. The "clean" points can be changed to "potential" or "infected" points according to the test results of people who passed by these points. The "potential" or "infected" points can be changed into "clean" points according to the life cycle of the virus on surfaces or places. For example, if a virus can live on surface for 48 hours only, that means an "infected" or a "potential" point will be changed to a 'clean" point after 48 hours.

Figure 7:
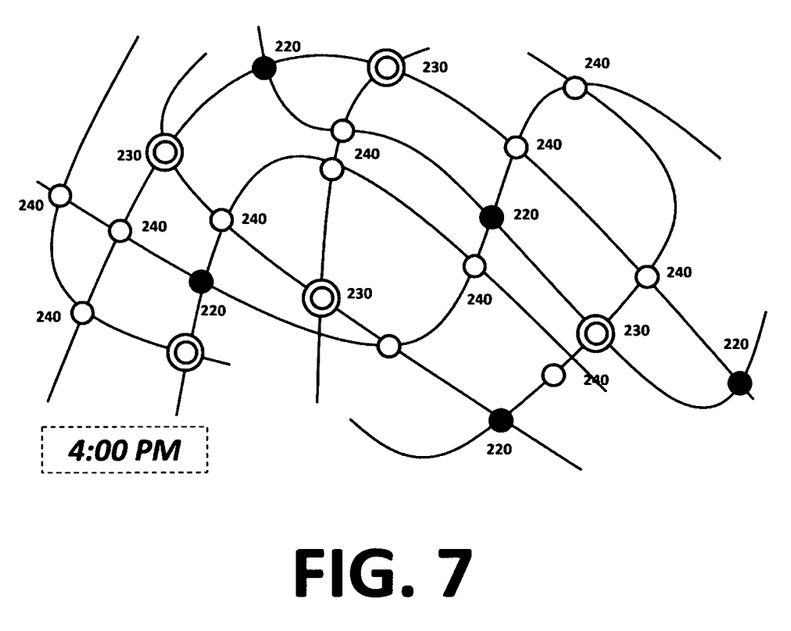
FIGS. 7 to 9 illustrate an example of a coronavirus real-time map at three different times during the same day.

The graphical representation of the "clean", "potential" and "infected" points over a period of time generates a coronavirus real-time map. For example, FIG. 7 illustrates a coronavirus real-time map at 4:00 PM on a certain day. As shown in the figure, the black circle 220 represents an "infected" point, the two white circles represent a "potential" point, and the single white circle represents a "clean" point. The real-time map means the tags of the points can change from "clean" to "potential" or "infected" or vice versa at any time. This change is based on the virus test results of the people who pass by these points, and the life cycle of the virus as mentioned previously.

Figure 8:
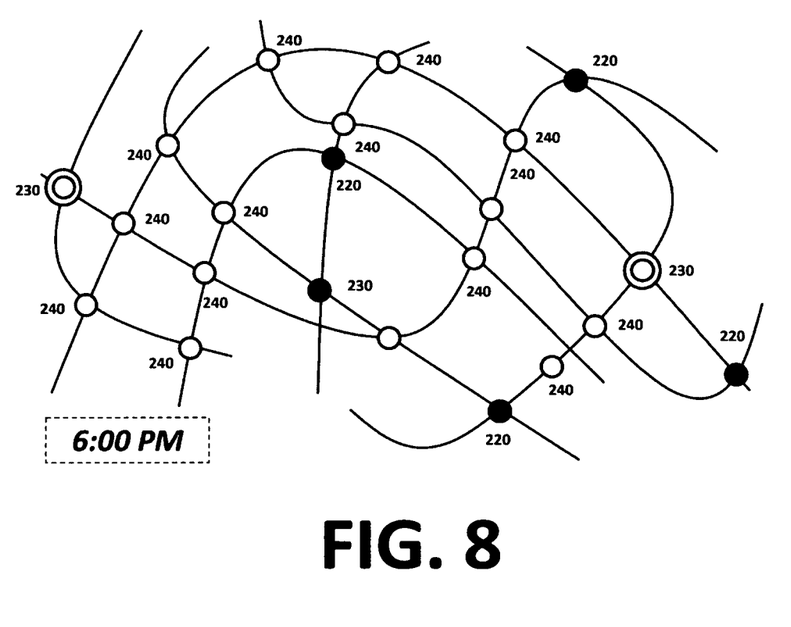
Figure 9:
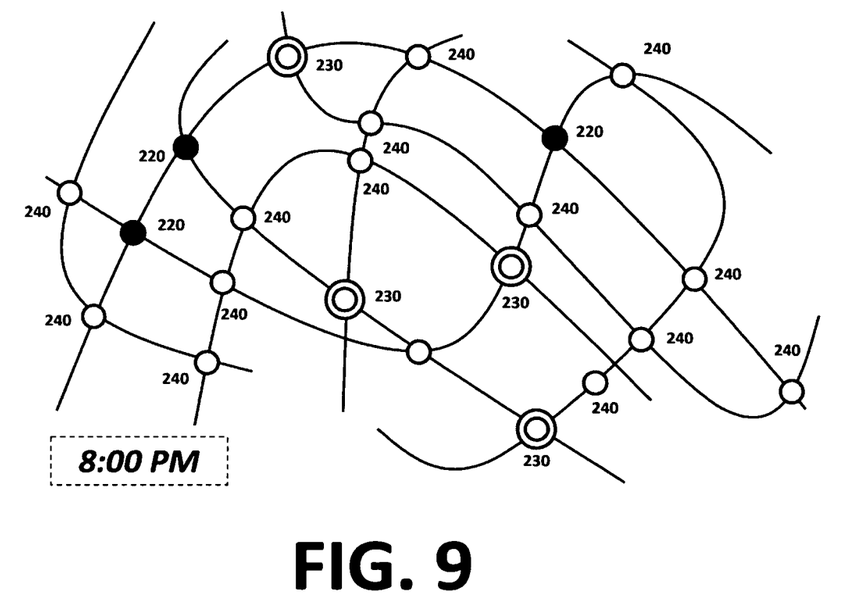

FIGS. 8 and 9 illustrate the same coronavirus real-time map, of FIG. 7, at two different times, 6:00 PM and 8:00 PM of the same day. As shown in the previous three figures, the "clean", "potential" and "infected" points are changing from time to other according to the virus test results of the people who pass by these three points, and the life cycle of the virus. According to this real-time map that contains 22 points, each point has one of three probabilities, "clean", "potential" or "infected", accordingly, the number of different options of this map equals 31,381,059,609 option.

Figure 10:
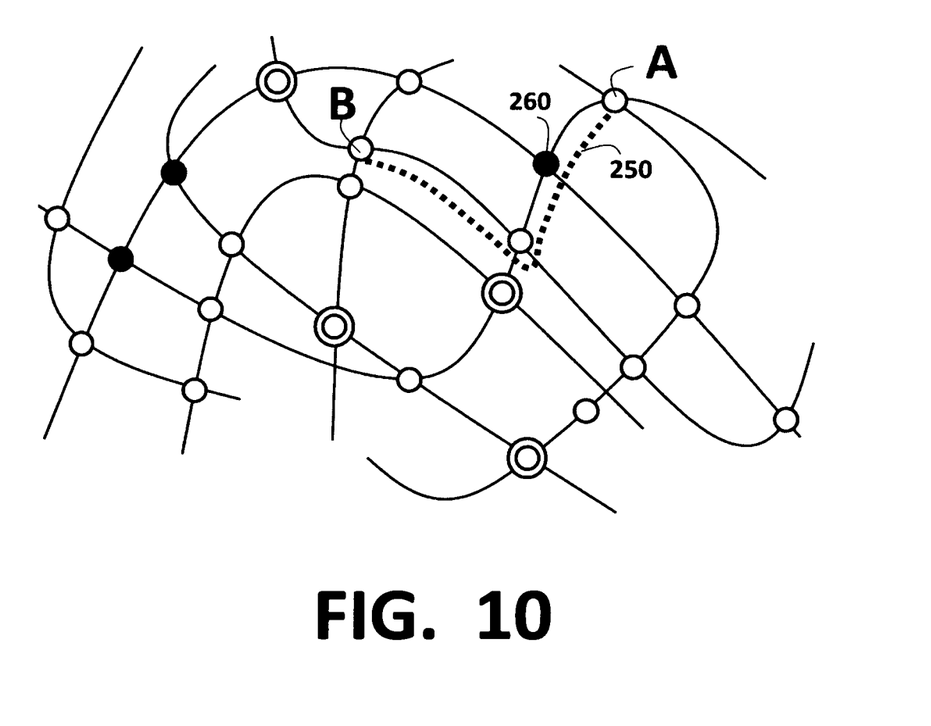
FIGS. 10 to 12 illustrate routing options for a user to move from a start point to an end point without passing by infected points or areas.
Figure 11:
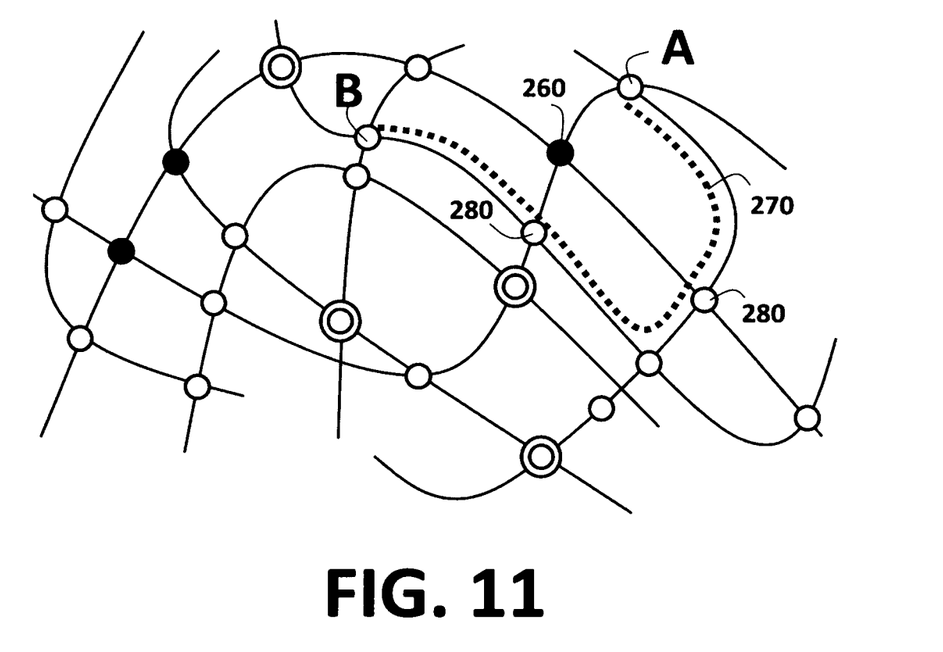
Figure 12:
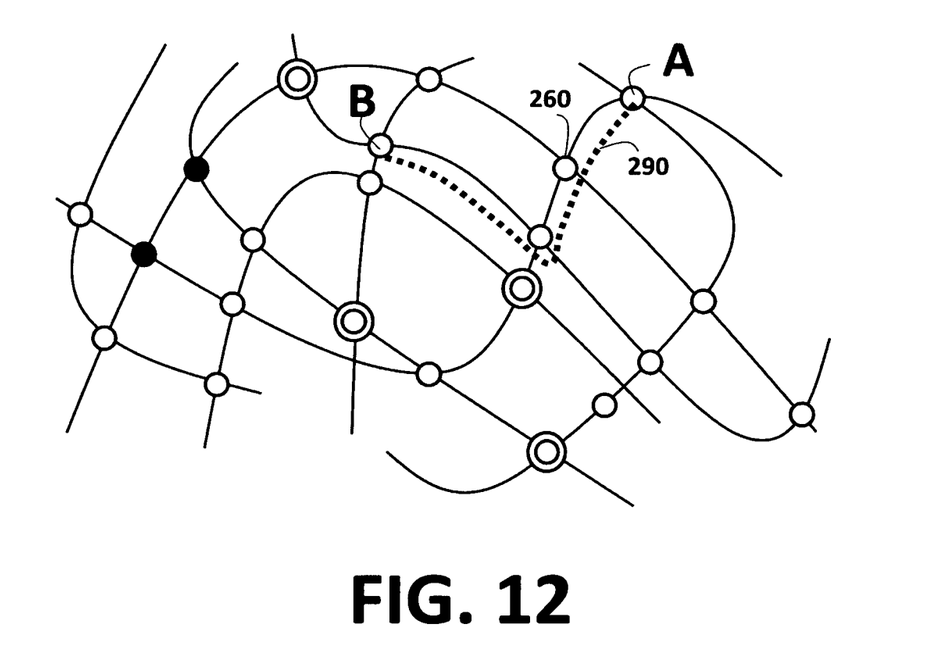

Generally, the previous coronavirus real-time map can be utilized with a Global Positioning System "GPS" to provide real-time routing directions related to the infected spots or areas. For Example, FIG. 10 illustrates a traditional route 250 to move from point "A" to point "B" on the map. As shown in the figure, this route passes by one of the "infected" points 260. FIG. 11 illustrates a recommended route 270 to move from point "A" to point "B" while avoiding passing by the "infected" point 260. As shown, this route only passes by "clean" points 280. FIG. 12 illustrates changing the route 290 to its original route of FIG. 10, once the "infected" point is changed to a "clean" point", based on the life cycle of the virus.

It is important to note that the intersection point can be generated from more than two paths of more than two users. The greater the number of people who tested positive after passing by an intersection point the greater the possibility of this intersection point to be an infected point. Generally, the intersection point could be an area or location that people visit or use. The restaurants, coffee shops, gums, movie theatres, schools, or the like are all examples of intersection points that usually used by two or more users.

In one embodiment of the present invention, the coronavirus real-time map provides a safe route to move from a location to other without passing by infected areas. If there is no option but passing by an infected area, the present invention generates an alarming message for the user to be careful while passing by such infected locations. In another embodiment, the present invention estimates the life cycle of the virus at an infected area, and askes the user to reschedule their visit to this area after certain time. This is to ensure that the "infected" points are changed to "clean" points after this certain time.

The history of the points of the coronavirus real-time map can provide a predication for the future of these points. For example, a "clean" point that was previously tagged multiple times as an "infected" point has a high potential to be an "infected" point in the future. In addition, an "infected" point that used to be a "clean" point for a long time has a high potential to be a "clean" point in the future. This type of future predication is useful when there is no data collected about some points or areas, which makes the present invention predict in a scientific manner.

The points of a coronavirus real-time map that share similar parameters can also share a similar future predication. For example, the points that have the same number of paths intersections, or located in a similar environment, if one of them became "infected" point, there is a potential that the other similar points will become an "infected" points in the future. This way of analysis provides the present invention another way of future predication based on the similarity of the collected data and geographic locations or environment of the points.

To create a coronavirus real-time map, the present invention does not require tracking the user's routes or geographic locations. This is to secure the personal privacy of the user which is one of the main benefits of using the present invention. To achieve that, the present invention utilizes the GPS on the user's mobile phone to track their geographic locations without sending this data anywhere. In other words, this data is locally stored on the user's mobile phone without giving anyone access to it. Once the user tested positive for coronavirus, their historical data are released to update the coronavirus real-time map, creating new "infected" points.

The coronavirus real-time map can be in the form of a software program installed on the user's mobile phone to be updated every time an intersection point is changed to be a "clean", a "potential" or an "infected" point. This update does not reveal any information about the users who were tested positive for coronavirus to secure their personal privacy. In addition, the user who tested positive will never reveal any tracking data until the test result is released. The users who tested negative for the virus do not need to send their tracking information to the system. As mentioned previously, the tracking of the user's location is done by the GPS of the user's mobile phone.

According to the aforementioned description, in one embodiment, the present invention discloses a method of creating a virus real-time map. This method comprises; detecting the movement paths of multiple users who tested positive for the virus; locating the infected points of intersections of the movement paths; updating the infected points of intersections according to the life cycle of the virus; and providing the user with instructions when approaching the infected points of intersections.

In another embodiment, the present invention discloses a system for virus alarming. This system comprises; a tracking unit that detects and stores the geographic positions of a user; a reporting unit that sends the history of the user's geographic positions to a central unit once the user is tested positive for the virus; a central unit that detects the infected points of intersections according to the data received from the reporting unit; and an alarming unit that alarms the user when approaching an infected point of intersection.

Figure 13:
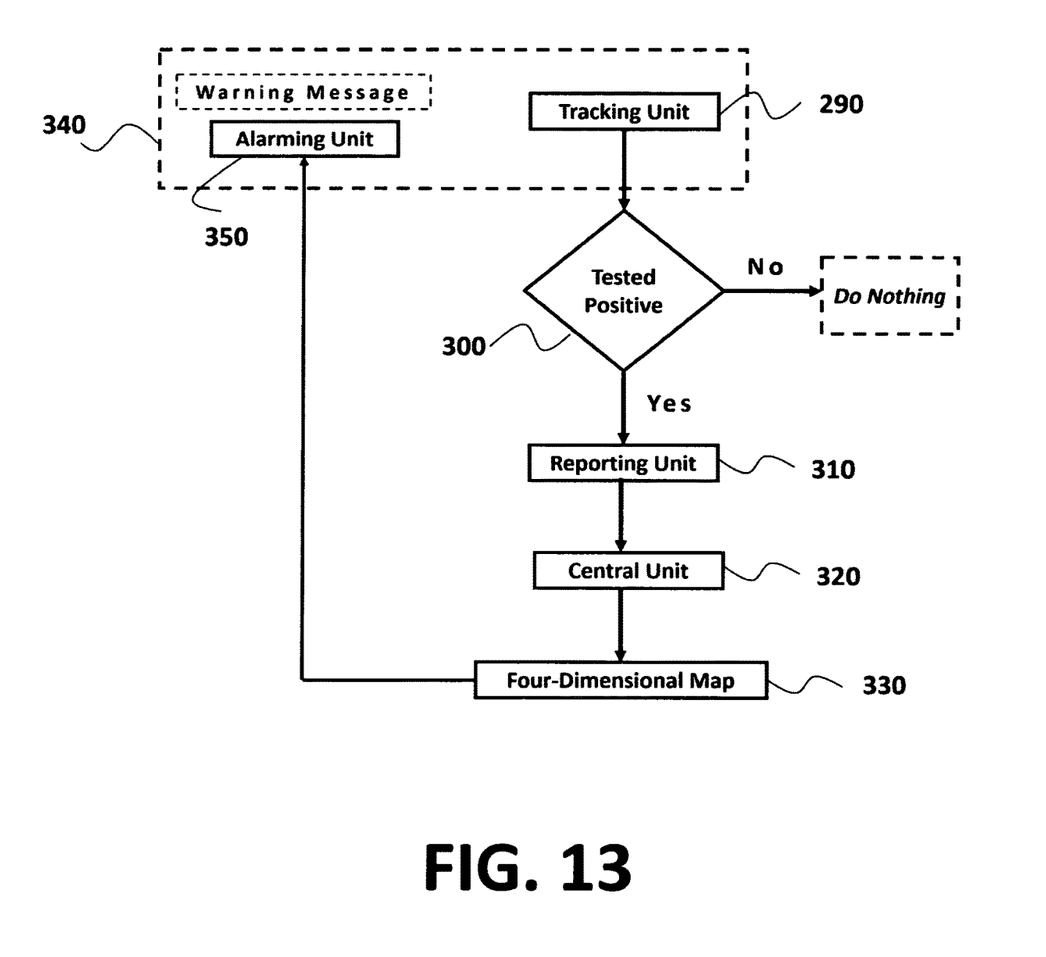
FIG. 13 illustrates a block diagram for the system of the present invention according to one embodiment.

FIG. 13 illustrates a block diagram showing the system of the present invention according to one embodiment. As shown in the figure, the system is comprised of a tracking unit 290 that tracks and locally stores the geographic position of the user. When the user is tested positive for a virus, as block 300 indicates, the data representing the history of the geographic positions of the user is sent by the reporting unit 310 to a central unit 320. The central unit updates the infected locations on a four-dimensional map 330, and sends this update to the user's mobile phone 340. Once the user approaches one of the infected locations, an alarming unit 350 generates a warning message to the user. The tracking unit and the alarming unit are two software programs installed on the user's mobile phone. As shown in the block diagram, when the user is tested negative for the virus, the tracking unit does not send any data to the reporting unit.

The invention claimed is:

1. A method of creating a virus real-time map comprising:
    detecting the movement paths of multiple users who tested positive for the virus;
    identifying infected points at intersections of the movement paths;
    updating the status of the infected points at intersections according to the life cycle of the virus, wherein the status of the infected points is predicated based on the status of similar infected points; and
    providing users with instructions for avoidance when approaching the infected points of intersections.

2. The method of claim 1, wherein the movement paths represent the historical geographic locations of the users over a period of time.

3. The method of claim 1, wherein the movement paths are detected using a Global Positioning System (GPS).

4. The method of claim 1, wherein the infected points are defined as the points of intersection between the paths of two users who have both tested positive for the virus.

5. The method of claim 1, wherein updating the infected points involves changing the status from 'infected' to 'non-infected'.

6. The method of claim 1, wherein the life cycle of the virus is defined as the period during which the virus remains viable and capable of infection on a surface.

7. The method of claim 1, wherein the instructions provided to the user are in the form of sound representations or visual representations of information.

8. The method of claim 1, wherein a new path option is provided to enable the user to reach a final destination without passing by an infected point of intersection.

9. The method of claim 1, wherein the status of an infected point is determined based on the historical data of the infected point.

10. The method of claim 1, wherein the status of the infected points is predicated based on the status of similar infected points for the same virus.

11. The method of claim 1, wherein the method is executed on an electronic device, such as a mobile phone, which is equipped with a Global Positioning System (GPS) for detecting the movement paths, and a computer program for updating the infected points and providing the user with instructions.

12. The method of claim 11, wherein the data of the movement paths is locally stored on the user's electronic device and is only released when the user tests positive for the virus.

13. The method of claim 11, wherein the electronic device is equipped with a digital screen to present graphical instructions to users.

* * * * *